United States Patent [19]

Andersson et al.

[11] 4,168,300

[45] Sep. 18, 1979

[54] METHOD OF REMOVAL OF HEPATITIS VIRUS

[75] Inventors: Lars-Olov Andersson, Knivsta; Håkan G. Borg, Huddinge; Gudrun M. Einarsson, Upsala, all of Sweden

[73] Assignee: AB Kabi, Stockholm, Sweden

[21] Appl. No.: 702,666

[22] Filed: Jul. 6, 1976

[30] Foreign Application Priority Data

Jul. 9, 1975 [SE] Sweden .............................. 7507854
May 8, 1976 [SE] Sweden .............................. 7605632

[51] Int. Cl.$^2$ ..................... A61K 39/12; C12K 5/00
[52] U.S. Cl. ........................................ 424/12; 424/89; 210/29; 210/64; 260/112 R; 260/112 B; 435/239
[58] Field of Search ..................... 210/24, 29, 59, 64, 210/501; 424/12, 79, 81, 84, 89; 260/112 B, 112 R; 195/1.5

[56] References Cited

U.S. PATENT DOCUMENTS

| 3,425,962 | 2/1969 | Granatek | 424/79 |
|---|---|---|---|
| 3,636,191 | 1/1972 | Blumberg | 424/89 |
| 3,836,433 | 9/1974 | Wirth | 424/12 |
| 3,852,157 | 12/1974 | Rubenstein | 424/12 |
| 3,951,937 | 4/1976 | Vnek | 424/89 |
| 3,976,767 | 8/1976 | Neurath | 424/89 |
| 3,991,018 | 11/1976 | Strop | 210/24 |
| 3,992,517 | 11/1976 | Lowke et al. | 424/89 |
| 3,994,870 | 11/1976 | Neurath | 424/89 |
| 4,000,098 | 12/1976 | Hofstee | 260/112 R |

OTHER PUBLICATIONS

Chemical Coupling of Enzymes to Cross-Linked Dexiran, Axen & Porath, Nature, Apr. 1966, pp. 367-369.
Abstracts of the Annual Meeting of American Society of Microbiology, 1976, pp. 246-247.
Journal of Infectious Diseases, vol. 128, 1973, Nollingen, pp. 753-760.
Journal of Virology, vol. 16, No. 3, 1975, pp. 508-515.
Isolation of Aleutian Mink Disease Virus by Affinity Chromalography, Science, 12 Jan., 1973, 187-189.
Hackh's Chemical Dictionary, Grant, Fourth Edition, McGraw-Hill, 1972, pp. 130, 330, 634.

Primary Examiner—Charles W. Hart
Assistant Examiner—Ernest G. Therkorn
Attorney, Agent, or Firm—A. A. Orlinger

[57] ABSTRACT

Hepatitis virus is removed from a biological material contaminated with the virus by contact with a preparation. The preparation may be agarose gel or beaded polyacrylamide plastic coupled with a variety of hydrophobic ligands.

1 Claim, No Drawings

METHOD OF REMOVAL OF HEPATITIS VIRUS

This invention is that of methods for removing or concentrating hepatitis virus from biological materials containing that virus.

More specifically, preparations used in these methods with an affinity for hepatitis virus are composed of a water-insoluble, water-permeable, preferably cross-linked gel-matrix substance, onto which is coupled, directly or through an intervening spacer (i.e. a molecule extender), a hydrophobic ligand which has an aliphatic chain moiety with more than seven carbons or a condensed ring system (i.e. nucleus).

The method of concentrating, which actually amounts to removing, hepatitis virus from such hepatitis contaminated biological materials comprises the essential step of bringing such virus contaminated material in contact with a preparation as just earlier described.

Hepatitis virus type B, also known as serum hepatitis virus, is spread by its presence in such biological material as blood, plasma, plasma fractions, plasminogen, serum, urine and feces. Type B hepatitis virus thus may be spread, for example, by plasma fractions used for therapeutic purposes.

This virus may be present in sewage water and other kinds of sewage comprising biological material that contains that virus in sufficient amount to spread the disease. Hepatitis virus type B then can be detected by immunological methods relating to the structure of the viral surface antigen, $HB_sAg$, which antigen is also known as Australia antigen, and briefly as Au-antigen.

The methods of detecting Au-antigen, that were used in the work on the present invention are (i) Ausria II 125, radio-immunology assay test kit, of Abbott Laboratories, North Chicago, Illinois, U.S.A.; (ii) Hepanosticon, reversed hemagglutination assay test kit, Organon, of Oss, Holland; (iii) Immunodiffusion, ID, Berg et al., Vox Sang. Vol. 22 (1972) p. 1.; and (iv) Immunoelectro-osmoforesis, IEOP, Hansson and Johansson, Vox Sang. Vol. 21 (1971), p. 531.

When used for testing blood samples, the Ausria test shows the highest sensitivity, but in assaying fractions of biological material the accuracy increases in the evaluation of the effect of the steps conducted if additional tests are carried out utilizing another assay system.

By relying in hospital routine only on approved blood donors who are hepatitis negative, as shown by the most sensitive assay method, it is possible to reduce the risk of hepatitis transmission considerably. However, as a result a substantial part of the available quantities of blood is not utilized. Thus, substances adaptable to industrial scale technology as well as a method suitable in industrial plasma fractionation, for selective removal of hepatitis virus preserves for hospitals an enhanced supply of blood serum, plasma, and plasma fractions.

Even though the assay sensitivity has been substantially improved by the radio-immunoassay technique, there still remains a risk of this hepatitis virus being present in blood, plasma, and plasma fractions in spite of a negative assay result.

Concentrating hepatitis virus by the method of the present invention makes possible testing of highly concentrated samples, whereby the accuracy of the hepatitis assay system used is greatly improved.

At an August 1972 meeting of the American Chemical Society (at New York, N.Y., U.S.A.) S. E. Charm and B. L. Wong described a method for removing hepatitis virus from blood plasma by using gel-bound antibodies against hepatitis virus. This study was published in Biotech. Bioeng., vol. 16 (1974) p. 593. Technical scale use of their method is reduced severely by the limited supply of these antibodies.

In addition, the risk of leakage of immunogenic material from the antibody carrier must be considered to the extent that the method is adapted to the fractionation of plasma of human origin and that the resulting plasma fractions are to be used in hospitals.

The new method of the invention lack the drawbacks of the earlier known technique. The preparations used in the new method (i) are easily applicable to production on a technical scale utilizing readily applicable synthesis steps, and (ii) comprise no immunogenic material. The affinity of the preparations of the invention for hepatitis virus is high and specific, and the reaction between these preparations and hepatitis virus is rapid and irreversible. Thus, there is no risk of leakage of this virus in the handling of these new preparations after hepatitis virus has been bound onto or to them.

The preparations used in this invention comprise a water-permeable matrix material, e.g. a water-insoluble gel, such as a high molecular weight carbohydrate (of at least 1000 mol. wt.) or plastic material such as a polyacrylamide (including sufficient, as at least about 0.1%, of N,N'-methylene-bis-acrylamide copolymer to retain bead form) carrying, if desired by the intervention of a spacer incorporated into the matrix, a hydrophobic ligand having a carbon chain of more than seven carbon atoms or a condensed ring system.

The active preparations or substances used in the invention are provided by coupling the selected ligand to the gel-forming matrix material.

All of the divalent, covalent coupling groups studied, namely, (i) $-O-\underset{\underset{NH}{\|}}{C}-NH-$,  (ii) $-O-\underset{\underset{NH}{\|}}{C}-NH-NH-$, (iii) $-NH-(CH_2)_{2 \text{ to } 6}-NH-$, (iv) $-C-O-NH-$, or (v) $-NH-CO-$ proved equivalent, and to be strictly subordinated to the structure of the ligand, from a performance point of view.

Also, the type of constitution of the water-permeable matrix material, for example, a polyamide plastic such as a polyacrylamide, or a carbohydrate matrix of the character earlier above noted, such as agarose—and if desirable cross-linked by bisepoxide, glutaric dialdehyde, divinylsulfone, dibromopropanol, or epichlorhydrin—is of less importance than the ligand.

Highly influential for providing the affinity of the preparations of the invention for the hepatitis virus is the hydrophobic character of the ligand. That is demonstrated by the following table which summarizes test studies on removing hepatitis virus from human plasma contaminated by hepatitis:

Table

Binding Of Hepatitis Virus From Highly Au-positive Human Plasma

Table-continued

In these tabulated test results, the same gel-matrix material was used and only the ligand was changed. In the tests, the results from which are tabulated, the affinity of each of the various preparations of the invention for the hepatitis virus was assayed by the above-identified immunological assay methods. A strong and complete binding of hepatitis virus to a preparation of the invention used is recorded in the table as: — , to show that no hepatitis virus is detectable in the plasma test sample after treatment with a preparation of the invention. The symbol: + , designates an insignificant residual amount of heptatitis virus in the plasma sample; and ++ indicates an unchanged or slightly reduced amount of Au-antigen in the plasma sample after treatment.

| Ligand/carbon chain | Au-antigen in plasma sample after treatment |
|---|---|
| (Matrix used in this series was Sepharose 4B, a beaded agarose gel prepared by allowing a 4% aqueous solution of agarose to gel in bead form, product of Pharmacia Fine Chemicals, of Piscataway, New Jersey, U.S.A. and of Uppsala, Sweden): | |
| -hexylamine | ++ |
| -glycyl-norleucine | ++ |
| -glycyl-DL-phenylalanine | ++ |
| -cyclopentylamine | ++ |
| -cycloheptylamine | ++ |
| -phenylethylamine | ++ |
| -hexamethylene diamine (as spacer)-benzoic acid | ++ |
| -hexamethylene diamine (spacer)-heptanoic acid | ++ |
| -hexamethylene diamine (spacer)-succinic acid | ++ |
| -hexamethylene diamine (spacer)-phthalic acid | ++ |
| -octylamine | — |
| -decylamine | — |
| -dodecylamine | — |
| -octadecylamine | — |
| -hexamethylene diamine (spacer)-octylsuccinic acid | — |
| -cysteamine (spacer)-octylsuccinic acid (as in Ex. 11) | — |
| -hexamethylene diamine (spacer)-naphthylacetic acid (Ex. 12) | — |
| -hexamethylene diamine (spacer)-cholesterol hydrogen succinate (Ex. 13) | — |
| hexamethylene diamine (spacer)-cholic acid (Ex. 14) | — |

Note:
that in the case of all of the foregoing tests wherein the result was ++, the grouping that was coupled to the matrix-gel has less than eight carbons in its chain.

(Matrix used in this next series was SEPHAROSE-4B cross-linked in various ways, as seen in the respectively identified examples):

| Ligand | Au-antigen after treatment |
|---|---|
| -ethylenediamine(spacer)-octylsuccinic acid (as in Ex. 1) | — |
| -butylenediamine(spacer)-octylsuccinic acid (Ex. 1) | — |
| -hexamethylene diamine(spacer)-octylsuccinic acid (Ex.1) | — |
| -hexamethylene diamine(spacer)-dodecylsuccinic acid (Ex.2) | — |
| -caprylhydrazide (Ex. 3) | — |
| -tetradecylamine (Ex. 6) | — |
| -(2-amino-dodecane) (Ex. 7) | — |
| -ethylenediamine(spacer)-undeceene-10-acid (Ex. 8) | —. |
| (Matrix in this series was a polyacrylamide, from Bio-Rad Laboratories, 32nd and Griffin Avenue, Richmond, California 94804, U.S.A.): | |
| -propylene(spacer)-decylamine (as in Ex. 10) | —. |

The following examples illustrate, but without limiting, the invention:

EXAMPLE 1

Removal of Au-antigen from plasma by adsorption onto SEPHAROSE-4B-(ethylenediamine-octylsuccinic acid) conjugate:

Production of the agarose-spacer derivative: SEPHAROSE-4B (i.e. agarose) beads were activated by washing carefully 100 ml. of adequately sedimented SEPHAROSE-4B with water. The excess of the washing liquid thereafter was removed by suction filtration before the gel was transferred to a solution of 4 g. of cyanogen bromide in 100 ml. of distilled water. After equilibration for 15 min. while stirring and ice-cooling, the equilibrated agarose gel suspension was activated at pH 11 for 6 to 7 min. while the pH was kept constant by adding 4 M sodium hydroxide.

For coupling of the ethylenediamine(spacer) the thus activated gel was washed on a glass filter with cold 0.5 M sodium bicarbonate -carbonate solution of pH 9.8 before being transferred into a solution of 10 g. of ethylenediamine in 100 ml. of distilled water, the pH of which had been adjusted to 9.8 with concentrated hydrochloric acid. The reaction mixture then was left at room temperature while stirring for 20 hours. The resulting spacer-gel derivative was thoroughly washed.

25 ml. of the aqueous suspension of the resulting spacer-gel derivative was suspended in 20 ml. of dioxane. A fresh solution of 6 g. of octylsuccinic anhydride in 60 ml. of dioxane was added dropwise while stirring at room temperature. The pH was kept between 7.5 and 8 by adding a dilute sodium hydroxide solution. The resulting ligand-bearing adsorbent was thoroughly washed separately successively with dioxane, dioxane-water (2:1), water, 1 M sodium chloride, and a buffer (of pH 7.5) consisting of 0.05 M TRIS, 0.02 M sodium citrate and 0.10 M sodium chloride.

Replacing the ethylenediamine spacer used in this example by the molal equivalent amount of 1,4-diaminobutane and 1,6-diaminohexane separately respectively provides separately respectively each of the two resulting corresponding spacer-gel derivatives. Then reacting each of these spacer-gel derivatives with octylsuccinic anhydride as in this example provides separately each of the corresponding resulting gel-spacer-ligand conjugate adsorbents, agarose-1, 4-diaminobutane-octylsuccinic acid and agarose-1,6-diaminohexane -octylsuccinic acid.

Au-antigen test: A pool of Au-antigen positive plasma with a titer (given relative to a standard antigen) of 1:64 according to IEOP and 1:32 according to ID was used as starting material.

To each of 6 test tubes was added 2 ml. of this Au-antigen positive plasma and 2 ml. of a suspension of 3 parts of the thoroughly sedimented adsorbent (of Example 1) equilibrated first with test buffer and then wetted with 1 part of the same buffer. The samples were shaken for 1, 2, 5, 10, 20 and 30 min. separately respectively, and the equilibrated adsorbent gels then were separated by centrifugation. Each supernatant was assayed for Au-antigen and found negative according to ID, IEOP and Hepanosticon.

EXAMPLE 2

Removal of Au-antigen from plasma in adsorption to SEPHAROSE-4B-(hexamethylene diamine-dodecyl-succinic acid) conjugate:

Production of the gel-spacer derivative: For cross-linking the SEPHAROSE-4B, 100 ml. of it was mixed with 2 ml. of epichlorhydrin and 0.5 g. of sodium borohydride. The mixture was vigorously agitated at 60° C. for 1 hour. The cross-linked gel was thoroughly washed with warm water and mixed with a solution of 0.25 g. of sodium borohydride dissolved in 50 ml. of 2 M sodium hydroxide. The mixture was autoclaved at 120° C. for 1 hour. Then the gel was washed with an alkaline sodium borohydride solution. Concentrated acetic acid was added slowly until the pH of the mixture approached 4. Finally, the gel was washed with a substantial volume of water to wash out all water-soluble products.

Production of the SEPHAROSE-hexamethylene diamine spacer-gel was conducted using hexamethylene diamine in a procedure following that of Example 1.

25 ml. of the resulting hexamethylene diamine spacer-gel derivative was transferred to a glass filter and washed with dioxane-water (2:1) before being suction dried and transferred to a fresh solution of 1 g. of dodecylsuccinic acid and 1.5 g. of the water-soluble carbodiimide N-cyclohexyl-N'-[beta-(N-methylmorpholinoethyl)]-carbodiimide-p-toluene sulfonate in 60 ml. of dioxane-water (2:1). The mixture was stirred at room temperature for an hour before being transferred to a glass filter and thoroughly washed separately successively with dioxane, dioxane-water (2:1), 1 M sodium chloride, water, and the test buffer. The washed residue on the filter was the spacer-gel-ligand conjugate.

Au-antigen test: Au-antigen positive plasma, titer 1:128 according to ID and IEOP was used as starting material. A column (diameter 1.6, height 1.0 cm.) was packed with the spacer-gel-ligand conjugate equilibrated in test buffer. 7 ml. of the Au-antigen positive plasma was pumped into contact with the spacer-gel, at a flow rate of 5 ml. per hour. The test buffer was added pump-wise until no more protein material was eluted, as checked by UV scanning. The eluate collected was negative according to ID, IEOP, and Hepanosticon. The eluate was concentrated (by pressure dialysis) 10 times and still was negative in the hepatitis tests.

EXAMPLE 3

Removal of Au-antigen from plasma by adsorption to SEPHAROSE-4B-caprylhydrazide conjugate:

Production of the spacer-gel derivative: Ethyl caprylate was converted into the corresponding hydrazide by hydrazinolysis, by initially admixing 10 ml. of this ethyl ester with 10 ml. of 98% hydrazine hydrate. Ethanol (22 ml.) was added as solvent, until the reaction mixture cleared, following which the solution was left at room temperature for 15 hours. The crystallized out resulting caprylhydrazide was filtered off and washed with ice water and then with aqueous methanol (1:1) of room temperature.

The SEPHAROSE-4B was activated as in Example 1, then washed with the solution of the coupling agent used in the activation, and then was vacuum filtered. The coupling was achieved by transferring the activated gel to 100 ml. of a saturated solution of the caprylhydrazide in equal parts of dimethylformamide (DMF) and 0.2 M sodium bicarbonate. The pH was left unchanged during the coupling reaction which took place while stirring at room temperatue for 15 hours. The resulting SEPHAROSE-4B-caprylhydrazide conjugate product was thoroughly washed separately successively with DMF, DMF-water (1:1), 1 M sodium chloride, water, and the test buffer.

Au-antigen test: Au-antigen positive plasma, titer 1:128 according to ID and IEOP, was used as starting test material. To 2 ml. of a suspension consisting of 3 parts of thoroughly sedimented SEPHAROSE-4B-caprylhydrazide conjugate (the adsorbent) equilibrated with the test buffer and 1 part of the same buffer were added 2 ml. of Au-antigen positive plasma. The mixture was gently agitated for 30 min. and the gel-ligand conjugate was separated by centrifugation. The supernatant was negative for Au-antigen according to ID, IEOP and Hepanosticon.

EXAMPLE 4

Removal of Au-antigen from albumin solution by adsorption to Agarose-(ethylenediamine-octylsuccinic acid) conjugate:

Production of the gel-spacer derivative and ligand conjugate: The agarose gel-ethylenediamine-octylsuccinic acid conjugate was prepared by a procedure following that in Example 1.

Au-antigen test: Au-antigen positive albumin solution, titer 1:64 according to ID and IEOP and obtained by fractionating Au-antigen positive plasma, was used as the starting test material. The adsorption was conducted batchwise following the procedure according to Example 3. The supernatant was tested for Au-antigen and found negative according to ID, IEOP and Hepanosticon.

EXAMPLE 5

Removal of Au-antigen from a blood congulation factor concentrate by adsorption to SEPHAROSE-4B-(ethylenediamine-octylsuccinic acid) conjugate:

Production of the gel-spacer derivative and ligand conjugate: The gel-spacer derivative and ligand conjugate were prepared by a procedure following that of Example 1.

Au-antigen test: An Au-antigen positive plasma was used for fractionating from it a concentrate comprising the coagulation factors II, VII, IX and X. A 1% protein solution of this concentrate was prepared and found to have an Au-antigen titer 1:32 according to ID. To a glass filter carrying a bed of 5 ml. of the gel-ligand conjugate equilibrated in the test buffer, were added 10 ml. of the protein test solution and the gel-ligand conjugate was washed 3 times with 5 ml. of the test buffer. The resulting combined eluates were assayed for Au-antigen according to ID, IEOP and Hepanosticon and found to be negative.

EXAMPLE 6

Removal of Au-antigen from plasma by adsorption to SEPHAROSE-tetradecylamine conjugate:

Production of the gel-ligand conjugate: SEPHAROSE-4B was activated as in Example 1.

For the coupling reaction, 100 ml. of cyanogen bromide activated SEPHAROSE-4B, which had been equilibrated with 95% ethanol and suction dried, was added to a solution of 22 g. of tetradecylamine in 100 ml. of 95% ethanol. The mixture was left at room temperature while stirring for 48 hours. The gel-ligand conjugate was thoroughly washed separately successively with warm 95% ethanol, aqueous ethanol (1:1), 1 M sodium chloride, water, and the test buffer.

Au-antigen test: Au-antigen positive plasma, titer 1:128 according to ID and IEOP was used as the starting test material. To a glass filter carrying a bed of 10 ml. of the spacer-gel-ligand conjugate equilibrated in the test buffer were added 35 ml. of Au-antigen positive plasma. The material was washed 3 times with 10 ml. of test buffer. The resulting combined eluates were assayed for Au-antigen and found negative according to ID, IEOP, Hepanosticon, and Ausria.

EXAMPLE 7

Removal of Au-antigen from plasma by adsorption to SEPHAROSE-4B-(2-amino-dodecane) conjugate:

Preparation of the agarose-2-amino-dodecane conjugate: 2-dodecanone was converted to the corresponding amine by reaction with hydroxylamine resulting in the corresponding oxime, followed by catalytic hydrogenation and elimination of water. The SEPHAROSE-4B used was equilibtated as in Example 1.

For coupling, 100 ml. of the cyanogen bromide activated gel, washed with 95% ethanol and suction dried, were added to a solution of 10 g. of 2-amino-dodecane in 100 ml. of 95% ethanol.

The mixture was left while stirring at room temperature for 48 hours, following which the agarose-2-amino-dodecane conjugate was thoroughly washed separately consecutively with warm 95% ethanol, aqueous ethanol (1:1), 1 M sodium chloride, water, and the test buffer.

Au-antigen test: Au-antigen positive plasma, titer 1:128 according to ID and IEOP, was used as starting test material. The test was run as in Example 3 and the supernatant was found to be Au-antigen negative when assayed according to ID, IEOP and Hepanosticon.

EXAMPLE 8

Removal of Au-antigen from plasma by adsorption to SEPHAROSE-(ethylenediamine-undeceene-10-acid) conjugate:

Production of the spacer-gel-ligand conjugate: The SEPHAROSE-4B-ethylenediamine was produced, as in Example 1. To a fresh solution of 1.85 g. undecylenic acid and 2.1 g. of dicyclohexylcarbodiimide dissolved in 100 ml. of dioxane were added 100 ml. of SEPHAROSE-4B-ethylenediamine spacer-gel following its equilibration with dioxane and vacuum filtration. The SEPHAROSE-4B-ethylenediamine (spacer) suspension was left while stirring for 15 hours at room temperature and then washed separately consecutively with dioxane, dioxane-water (1:1), 1 M sodium chloride, and the test buffer, resulting in the SEPHAROSE-ethylenediamine (spacer)-undeceene-10-acid conjugate.

Au-antigen test: Au-antigen positive plasma, titer 1:128 according to ID and IEOP was used as starting test material. The test was run as in Example 3. The supernatant was found Au-antigen negative according to ID, IEOP and Hepanosticon.

EXAMPLE 9

Removal of Au-antigen from plasminogen concentrate by adsorption to SEPHAROSE-caprylhydrazide conjugate:

Production of the gel-ligand conjugate: The SEPHAROSE-4B-caprylhydrazide conjugate was obtained as in Example 3.

Au-antigen test: To 2 ml. of a plasminogen solution was added 0.5 ml. of highly Au-positive plasma, which mixture was found to be highly Au-positive according to ID and Ausria. This mixture was passed through a 4 cm. column loaded with 10 ml. of the gel-caprylhydrazide conjugate equilibrated with the test buffer. Fractions were collected and tested as in prior examples. The plasminogen-containing eluate was found to be negative when assayed according to ID and Ausria.

EXAMPLE 10

Removal of Au-antigen from plasma by adsorption to a copolymer of acrylamide (95%) and N,N'-methylene-bis-acrylamide (5%)-(propylene-decylamine) conjugate:

Production of the polyacrylamide (95%:5%) copolymer gel derivative: Polyacrylamide gel beads, e.g. BIO-GEL P 300 (copolymer of 95% acrylamide and 5% of N,N'-methylene-bis-acrylamide, product of Bio-Rad Laboratories, supra) briefly called "polyacrylamide copolymer" were left to swell in water and then thoroughly washed with 0.05 M sodium phosphate buffer (pH 7.0). For the activation treatment, 20 ml. of this swelled gel suspension in this buffer (0.5 of the dry gel per 25 ml. of buffer) were mixed with 5.0 ml. of glutardialdehyde and incubated at 37° for 18 hours. Thereafter, the thus activated polyacrylamide copolymer-propylene gel derivative was thoroughly washed separately consecutively with a phosphate buffer (pH 7.0) and dioxane-water (3:2) (pH 8.0).

The coupling was achieved by adding the dry gel to a solution of 3 g. of decylamine in 30 ml. of dioxane-water (3:2) (pH 8.0). The mixture was left while stirring at +4° C. for 18 hours following which the gel was washed with dioxane, dioxane-water (3:2), water, and test buffer.

Au-antigen test: Au-antigen positive plasma, titer 1:128 according to ID and IEOP, was used as starting test material. The test was run as in Example 3. Upon testing the supernatant was found to be Au-negative according to ID, IEOP and Hepanosticon.

EXAMPLE 11

Removal of Au-antigen from plasma by adsorption to SEPHAROSE-4B-(cysteamine-octylsuccinic acid) conjugate:

Production of the gel derivative: The SEPHAROSE-4B-cysteamine was obtained by reduction of SEPHAROSE-4B-cystamine, prepared by a procedure following that of Example 1, with 0.05 M mercaptoethanol in 0.1 M carbonate buffer (pH 8.5) for one hour. The SEPHAROSE-cysteamine was washed extensively separately with the carbonate buffer, water, and finally dioxane. To a solution of 1.2 g. of octylsuccinic acid in 40 ml. of dioxane, a solution of 1.84 g. dicyclohexylcarbodiimide in 10 ml. of dioxane and 25 ml. of SEPHAROSE-cysteamine were added. After two hours with stirring at room temperature another 1.84 g. of dicyclo-hexylcarbodiimide was added. Two hours later, the gel-(spacer)-ligand was washed with dioxane. The reaction procedure was repeated and followed by extensive washing consecutively with dioxane, dioxane-water, water and 0.1 M carbonate (pH 8.5). Remaining thiol groups were blocked by treating the SEPHAROSE-(cysteamine-octylsuccinic acid) conjugate with 60 mg. of iodoacetamide for 45 minutes. Finally, that conjugate was washed with the test buffer.

Au-antigen test: Au-antigen positive plasma, titer 1:32 according to ID, was used as starting test material. The adsorption was carried out batchwise as in Example 3. The supernatant was tested for Au-antigen and found negative according to ID, IEOP and Hepanosticon.

The foregoing examples illustrate, but without restricting, the preparations of the invention wherein the hydrophobic ligand coupled to the gel-matrix substance has an aliphatic chain moiety having more than seven carbons.

The preparations of the invention wherein the hydrophobic ligand coupled to the gel-matrix substance includes a condensed ring system (i.e. nucleus or moiety) are illustrated by, but not to be restricted to, the following examples:

EXAMPLE 12

Removal of Au-antigen from plasma by adsorption to SEPHAROSE-4B-(hexamethylene diamine-naphthyl-1-acetic acid) conjugate:

Preparation of the gel derivative: The SEPHAROSE-hexamethylene diamine was prepared by a procedure following that of Example 1.

25 ml. of the resulting spacer gel (i.e. agarose-hexamethylene diamine) was transferred to a glass filter and washed with dioxane-water (3:2) before being suction dried and transferred to a fresh solution of 1.1 g. of naphthyl-1-acetic acid in 30 ml. of dioxane-water (3:2). To the resulting suspension of the spacer-gel with that acid 2.65 g. of the water-soluble carbodiimide, N-cyclohexyl-N'-[beta-(N-methylmorpholinoethyl)]-carbodiimide-p-toluene sulfonate was added while stirring. Then the pH was adjusted to 4.8 with dilute hydrochloric acid. After an hour at room temperature a further 2.65 g. of the water-soluble carbodiimide was added. The mixture was left for another hour while stirring before it was transferred to a glass filter and thoroughly washed separately consecutively with dioxane, dioxane-water (3:2), 1 M sodium chloride, water and the test buffer.

Au-antigen test: Au-antigen positive plasma with titer 1:32 according to ID and titer 1:64 according to IEOP was used as starting test material. The adsorption was carried out batchwise as in Example 3. The supernatant was tested for Au-antigen and found to be negative according to ID, IEOP and Hepanosticon.

EXAMPLE 13

Removal of Au-antigen from plasma by adsorption to SEPHAROSE-(hexamethylene diamine-cholesterol hydrogen succinate) conjugate:

Production of the spacer-gel derivative: The SEPHAROSE-hexamethylene diamine was prepared by a procedure following that of Example 1.

20 ml. of the resulting hexamethylene diamine(-spacer) gel was transferred to a glass filter and washed separately consecutively with dioxane, 10% triethylamine in dioxane, and dioxane again, before being suction dried and transferred to a fresh solution of 0.5 g. of cholesterol hydrogen succinate in 25 ml. of dioxane.

The reaction was started by the addition of 0.35 g. of dicyclohexylcarbodiimide dissolved in 1 ml. of dioxane. The coupling was performed while stirring at room temperature. After two hours an additional same portion of carbodiimide was added. Then two hours later the coupled gel, i.e., agarose-(hexamethylene diamine-cholesterol hydrogen succinate) conjugate, was washed extensively separately consecutively with dioxane, dioxane-water, water and finally with the test buffer.

Au-antigen test: Au-antigen positive plasma titer 1:64 according to ID and 1:128 according to IEOP was used as starting test material. The adsorption was conducted batchwise as in Example 3. The supernatant was tested for Au-antigen and found negative, according to ID, IEOP and Hepanosticon.

EXAMPLE 14

Removal of Au-antigen from plasma by adsorption to SEPHAROSE-(hexamethylene diamine-cholic acid) conjugate:

Production of the spacer-gel derivative: The SEPHAROSE-hexamethylene diamine was obtained by a procedure following that of Example 1.

The coupling of the cholic acid to the spacer-gel derivative (i.e. agarose hexamethylene diamine) was conducted as in Example 13 except that 0.5 g. of cholic acid (instead of cholesterol hydrogen succinate was dissolved in 100 ml. of dioxane.

Au-antigen test: Au-antigen positive plasma, titer 1:32 according to ID, was used as starting test material. The adsorption was achieved batchwise as in Example 3. The supernatant was tested for Au-antigen and found to be negative according to ID, IEOP and Hepanosticon.

In the conjugates wherein the ligand is an alkylamino group or the caprylhydrazido group, as in Examples 3, 6, 7 and 9, the ligand is linked to the cyanogen bromide activated agarose through the amino nitrogen of the alkylamino group.

Each of the water-soluble di-substituted carbodiimide-p-toluene sulfonate of Example 2 and the dicyclohexacarbodiimide of Example 8 can be replaced by an equivalent amount of any other substance including anyone of the divalent, covalent coupling groups identified in the second paragraph preceding the paragraph containing the heading "Table" above.

Any of these substances including any of these just referred to covalent binding groups can be used so long as the substance is compatible with the water-insoluble, water-permeable gel-matrix material. Such covalent coupling group containing substance is compatible with the matrix material so long as the substance containing the desired said covalent group does not significantly impair or destroy the adsorptive effectiveness of the matrix material.

Also, the glutardialdehyde of Example 10 can be replaced by any other of the activating cross-linking agents recited in the first paragraph preceding the paragraph containing the heading "Table" above.

In any of the examples and any of the herein indicated possible modifications of them, the hepatitis virus contaminated material from which it is desired to remove some or all of the hepatitis virus is kept in contact with a sufficient quantity of the hydrophobic ligand comprising water-insoluble, water-permeable cross-linked gel-matrix substance of the invention for a sufficient time to enable removing from any desired part to substantially all of the hepatitis virus from the starting contaminated material.

The expression "a polyacrylamide plastic" as used herein and in the claims embraces the polyacrylamide copolymer as described in the fourth paragraph preceding the paragraph containing the heading "Table" as well as the specific polyacrylamide copolymer used in Example 10.

While the invention has been explained by reference to the description of the various specific embodiments of it as in the several examples, it is understood that various substitutions and/or modifications can be made in any of the illustrative embodiments within the scope of the appended claims which are intended to cover also equivalents of those embodiments.

What is claimed is:

1. A method for removing hepatitis virus from a biological material contaminated with said virus, comprising the step of bringing said hepatitis virus contaminated material in contact with a preparation which is composed of a water-insoluble, water-permeable, cross-linked gel-matrix substance selected from (a) a high molecular weight water-insoluble, water-permeable adsorbent, gel-matrix-forming carbohydrate of at least 1,000 molecular weight inert to ethanol, dioxane, dimethylformamide, sodium hydroxide at pH up to about 8, 0.5 M $Na_2CO_3$ solution, acetic acid at pH 4, and 1 M NaCl, and (b) a beaded polyacrylamide plastic; and onto which gel-matrix substance, directly or through a divalent molecule extender group selected from cysteamine, propylene, and an alkylene diamine having from 2 to about 6 carbons in the alkylene chain, there is coupled a hydrophobic ligand selected from the alkylamino groups from octylamino to octadecylamino, and the dodecyl-2-amino and the caprylhydrazido groups through the amino nitrogen of the alkylamino group or the caprylhydrazido group respectively, heptanoic acid, an alkyl succinic acid from octylsuccinic acid to dodecylsuccinic acid, naphthylacetic acid, and cholesterol hydrogen succinate.

2. The method according to claim 1, wherein the water-permeable matrix substance is a beaded agarose gel or a polyacrylamide plastic.

3. The method according to claim 2, wherein said matrix substance is polyacrylamide.

4. The method according to claim 3, wherein said polyacrylamide is a conjugate with propylene-decylamine as the ligand.

5. The method according to claim 2, wherein the matrix substance is the beaded agarose gel.

6. The method as claimed in claim 5, wherein the ligand coupled to said gel-matrix is selected from the octylamino, decylamino, dodecylamino, tetradecylamino, octadecylamino, dodecylamino-2, and caprylhydrazido groups.

7. The method as claimed in claim 5, wherein the ligand coupled to said gel-matrix directly or with its intermediary linked extender group is selected from ethylenediamine-octyl succinic acid, butylenediamine-octylsuccinic acid, hexamethylenediamine-octylsuccinic acid, octylamine, decylamine, dodecylamine, octadecylamine, hexamethylenediamine-dodecyl succinic acid, caprylhydrazide, tetradecylamine, 2-amino-dodecane, ethylenediamine-undeceene-10 acid, cysteamine-octyl succinic acid, hexamethylenediamine-naphthyl-1-acetic acid, hexamethylenediamine-cholesterol hydrogen succinate, and hexamethylenediamine-cholic acid.

8. The method according to claim 7, wherein said agarose gel is a conjugate with caprylhydrazide as the ligand.

9. The method according to claim 7, wherein said agarose gel is a conjugate with tetradecylamine as the ligand.

10. The method according to claim 7, wherein said agarose gel is a conjugate with 2-amino-dodecane as the ligand.

11. The method according to claim 7, wherein the hydrophobic ligand is coupled to the gel-matrix substance through the intervention of a divalent molecule extender group.

12. The method according to claim 11, wherein said agarose gel is a conjugate with ethylenediamine-octylsuccinic acid.

13. The method according to claim 11, wherein said agarose gel is a conjugate with hexamethylenediamine-dodecylsuccinic acid.

14. The method according to claim 11, wherein said agarose gel is a conjugate with ethylenediamine-undeceene-10-acid.

15. The method according to claim 11, wherein said agarose gel is a conjugate with cyteamine-octylsuccinic acid.

16. The method according to claim 11, wherein said agarose gel is a conjugate with hexamethylenediamine-naphthyl-1-acetic acid.

17. The method according to claim 11, wherein said agarose gel is a conjugate with hexamethylenediamine-cholesterol hydrogen succinate.

18. The method according to claim 11, wherein said agarose gel is a conjugate with hexamethylenediamine-cholic acid.

* * * * *